United States Patent
Vastra

(10) Patent No.: US 7,524,992 B2
(45) Date of Patent: Apr. 28, 2009

(54) CARBON-CARBON BOND CREATION METHOD COMPRISING THE COUPLING OF A TRANSFERABLE GROUP AND AN ACCEPTOR GROUP

(75) Inventor: Johann Vastra, Montagny (FR)

(73) Assignee: Rhodia Chimie, Aubervilliers (FR)

( * ) Notice: Subject to any disclaimer, the term of this patent is extended or adjusted under 35 U.S.C. 154(b) by 121 days.

(21) Appl. No.: 10/569,941

(22) PCT Filed: Aug. 24, 2004

(86) PCT No.: PCT/FR2004/002186

§ 371 (c)(1),
(2), (4) Date: Feb. 28, 2006

(87) PCT Pub. No.: WO2005/023735

PCT Pub. Date: Mar. 17, 2005

(65) Prior Publication Data

US 2007/0010683 A1   Jan. 11, 2007

(30) Foreign Application Priority Data

Aug. 28, 2003  (FR) .................................. 03 10259

(51) Int. Cl.
*C07C 41/01* (2006.01)
*C07C 25/18* (2006.01)
*C07C 1/00* (2006.01)

(52) U.S. Cl. ........................ 568/642; 570/144; 585/469

(58) Field of Classification Search ....................... None
See application file for complete search history.

(56) References Cited

U.S. PATENT DOCUMENTS

2002/0183516 A1   12/2002   Denmark et al.

OTHER PUBLICATIONS

Dupont et al., Palladacycles-An Old Organometallic Family Revisited: New, Simple, and Efficient Catalyst Precursors for Homogeneous Catalysis, Eur. J. Inorg. Chem., vol. 2001, Issue 8, Aug. 2001, pp. 1917-1927.*

Hatanaka et.al., "Highly Selective Cross-Coupling Reactions of Aryl(halo)silanes with Aryl Halides: A General and Practical Route to Functionalized Biaryls", *Tetrahedron*, 1994, pp. 8301-8316, vol. 50, No. 28, Elsevier Science Ltd, Great Britain.

Hiyama, "How I came across the silicon-based cross-coupling reaction", *Journal of Organometallic Chemistry*, 2002, pp. 58-61, No. 653, Elsevier Science B.V., Amsterdam, The Netherlands.

Alonso et al., "Highly Active Oxime-Derived Palladacycle Complexes for Suzuki-Miyaura and Ullmann-Type Coupling Reactions", *J. Org. Chem.*, 2002, pp. 5588-5594, No. 67, American Chemical Society, Columbus, Ohio, USA.

Herrmann et al., "Palladacycles as Structurally Defined Catalysts for the Heck Olefination of Chloro- and Bromoarenes", *Angew. Chem. Int. Ed. Engl.*, 1995, pp. 1844-1848, vol. 34, No. 17, Verlag Chemie, Weinheim, Germany.

* cited by examiner

*Primary Examiner*—Rosalynd Keys
(74) *Attorney, Agent, or Firm*—Buchanan, Ingersoll & Rooney P.C.

(57) ABSTRACT

The invention relates to a carbon-carbon bond creation method comprising the coupling of a transferable group and an acceptor group. The inventive method comprises the following steps: a) activation of a siliceous compound bearing a transferable group by an activation agent; b) addition of an acceptor group-bearing derivative; and, simultaneously or in any consecutive order, c) addition of a palladacycle-type compound acting as a catalyst of the coupling reaction between the transferable group and the acceptor group with the creation of the carbon-carbon bond.

43 Claims, No Drawings

CARBON-CARBON BOND CREATION METHOD COMPRISING THE COUPLING OF A TRANSFERABLE GROUP AND AN ACCEPTOR GROUP

The present invention relates to a coupling process between a transferable group and an acceptor group by creation of a carbon-carbon bond in the presence of a catalyst of palladacycle type.

The coupling of organometallic nucleophiles with organic halides or sulfonates in the presence of a catalyst based on nickel, palladium or platinum is currently the most effective means for producing carbon-carbon bonds.

Such cross-coupling reactions give access to a great many products which serve the chemistry, agrochemistry, pharmaceutical or electronic markets and high performance products which are used, for example, in the preparation of liquid crystals, and the like.

Grignard reagents were the first organometallics employed with success in this type of reaction and subsequently many other nucleophiles derived from lithium, zinc, tin, titanium, and the like, were tested.

A major advance was made by Suzuki et al. (*J. Organomet. Chem.*, 1999, 675, 147) by introducing boronic acids into the coupling reaction and then Hiyama et al. (*J. Organomet. Chem.*, 2002, 653(1-2), 303) showed that organosilyl compounds, also compatible with a large range of functional groups, can under some conditions be coupled with organic halides in the presence of palladium catalyst and of an anionic activator.

The studies by C. Najera et al. (*J. Org. Chem.*, 2002, 67, 5588-5594) also describe coupling reactions of the type of those of Suzuki using catalysts of palladacycle type and arylboronic acids.

The advantage of the organosilyl derivatives lies in the fact that it is easy to prepare them from chlorosilanes. They are lower in cost and are more easily purified than organic boronic acids, which have a tendency to polymerize. In addition, the reaction effluents with organosilyl compounds present fewer problems than the reaction discharges with organoboronic acids, with regard to the environment and current regulations.

Patent application WO 01/94355 discloses a process for carbon-carbon coupling starting from silyl derivatives and from an organic electrophile in the presence of a basic nucleophilic anionic activator and of a catalyst which is a metal from Group 10. However, the process described in this patent application results in undesirable homocoupling by-products, which is harmful to the provision of compounds of very high purity for the applications defined above.

However, it is indicated that the formation of homocoupling by-products can be reduced by addition of phosphine derivatives to the reaction medium. However, their removal can present problems, both with regard to the difficulty in producing products of high purity and with regard to the treatment of the effluents before discharge to the environment.

In addition, the phosphines are relatively difficult to synthesize, are generally unstable and are expensive.

There consequently exists a need for a novel synthetic process which makes possible the creation of a carbon-carbon bond between a transferable group and an acceptor group which eliminates the disadvantages related to the processes of the prior art.

Thus, a first object of the present invention consists in providing a process for coupling a transferable group to an acceptor group by creation of a carbon-carbon bond without having recourse to compounds of boron type.

Another object of the present invention is to provide a process for coupling a transferable group to an acceptor group by creation of a carbon-carbon bond without having recourse to compounds of phosphine type.

A third object consists in preventing, or at the very least reducing, the formation of homocoupling by-products during the creation of a carbon-carbon bond in a process which is targeted at the coupling of a transferable group to an acceptor group.

A fourth object of the present invention is to reduce the amount of catalyst necessary for the creation of a carbon-carbon bond during a process for coupling a transferable group to an acceptor group.

A fifth object of the present invention is to obtain coupling of a transferable group to an acceptor group by creation of a carbon-carbon bond with kinetics which are substantially higher than those observed with the analogous coupling reactions available in the prior art.

The preparation of products from the coupling of a transferable group to an acceptor group by creation of a carbon-carbon bond with good yields, in particular greater than those observed with the analogous coupling reactions available in the prior art, also represents one of the objects of the present invention.

Yet other objects will become apparent in the account of the invention which follows.

It has now been discovered that the objects set out above can be achieved in all or in part by virtue of the process for coupling a transferable group to an acceptor group by creation of a carbon-carbon bond, which represents one of the subject matters of the present invention, set out in detail below.

Thus, the present invention relates first of all to a process for creating a carbon-carbon bond by coupling a transferable group to an acceptor group comprising the stages of:
  a) activation of a siliceous compound carrying a group which can be transferred by an activating agent;
  b) addition of a derivative carrying an acceptor group and, simultaneously or consecutively, in any order,
  c) addition of a compound of palladacycle type which acts as catalyst of the reaction of coupling the transferable group to the acceptor group by creation of said carbon-carbon bond.

The process can also be followed by a stage d) of separation, isolation and purification of the coupling product thus obtained.

The stage a) of activation of the siliceous compound is carried out in a medium comprising a solvent, preferably a polar solvent, in particular ethers, among which may be mentioned, as nonlimiting examples, dioxane, tetrahydrofuran, anisole, dibutyl ether, methyl tert-butyl ether, ethylene glycol diethyl ether, diethylene glycol diethyl ether or diisopropyl ether, dioxane and anisole being among the preferred solvents. Of course, mixtures of these solvents can be used in all proportions.

However, the solvent of the activation stage is not limited to polar solvents and it is also possible to use other solvents, such as, for example, aromatic solvents, it being possible for mixtures of these solvents to be used. Toluene is a possible representative of this category of solvents.

It also remains understood that mixtures of one or more solvents chosen from polar solvents with one or more other solvents, such as those defined, for example, in the preceding paragraph, can be used.

In the stage a) of activation of the siliceous compound, use is made of the activating agents commonly used and in particular of anionic nucleophilic compounds. Generally, this anionic nucleophilic compound is capable of releasing anions, for example hydroxide (OH⁻) ions, ions of alkoxide type, and the like, in the reaction medium.

Organic or inorganic fluorides may also be suitable as activating agents. Mention may be made, in this case, of alkaline earth metal fluorides, in particular potassium fluoride, and of tetraalkylammonium fluorides, for example tetrabutylammonium fluoride.

Preferably, the activating agent is chosen from hydroxides of alkali metals and alkaline earth metals, alkoxides, carbonates, amides, and their derivatives. For example, the activating agent can be chosen from sodium hydroxide, lithium hydroxide, potassium hydroxide, barium hydroxide, barium oxide, the potassium salt of hexamethyldisilazane (KHMDS), and the like.

Preferably, the activating agent used is an alkali metal hydroxide, in particular sodium hydroxide, in the solid form, for example in the form of finely milled pellets, or in the form of an aqueous solution.

As in the case of the reaction solvent, mixtures of activating agents can be used.

The amount of activating agent employed is such that the activating agent/siliceous compound molar ratio is generally between 1 and 8, preferably between 2 and 6, generally between 3 and 5, for example approximately 4.

According to an advantageous embodiment of the present invention, the siliceous compound which has to be activated is run into the solvent/activating agent mixture so as to keep the reaction temperature between 40° C. and 120° C., preferably between 60° C. and 110° C., more preferably between 80° C. and 110° C.

It is obvious that the reaction medium can be heated or cooled, as the case may be, as the siliceous compound is being run in, so that the temperature of the reaction medium remains within the range of values which are set out above. The reaction medium can be cooled or heated according to any conventional method known to a person skilled in the art who is an expert in organic syntheses.

According to one aspect of the invention, the siliceous compound carrying the transferable group can be of any type and in particular a dihalosilane corresponding to the formula (I):

$$\begin{array}{c} R^T \diagdown \phantom{Si} \diagup X^1 \\ Si \\ R \diagup \phantom{Si} \diagdown X^2 \end{array} \quad (I)$$

in which:
$X^1$ and $X^2$, which are identical or different, are, independently of one another, a halogen atom selected from fluorine, chlorine, bromine and iodine, preferably from chlorine and bromine; more preferably, $X^1$ and $X^2$ are identical and are each a bromine atom or a chlorine atom, advantageously a chlorine atom;
R is selected from the hydrogen atom, a linear or branched alkyl radical comprising from 1 to 6 carbon atoms and the $R^T$ radical defined above;
$R^T$ is the transferable group and is selected from an aryl, vinyl and allyl radical, it being possible for each of them optionally to be substituted, $R^T$ preferably representing an optionally substituted aryl radical, for example an optionally substituted phenyl radical.

The transferable group $R^T$ can, for example, be a group of following formula $R'^T$:

$$\begin{array}{c} R^{T2} \phantom{==} R^{T3} \\ \diagdown \phantom{==} \diagup \\ \diagup \phantom{==} \diagdown \\ R^{T1} \end{array} \quad (R'^T)$$

in which:
$R^{T1}$, $R^{T2}$ and $R^{T3}$, which are identical or different, are selected, independently of one another, from the hydrogen atom and a hydrocarbon group having from 1 to 20 carbon atoms which can be a saturated or unsaturated and linear or branched aliphatic group; a saturated, unsaturated or aromatic, monocyclic or polycyclic, carbocyclic or heterocyclic group; or a sequence of aliphatic and/or carbocyclic and/or heterocyclic groups as mentioned above.

The invention does not rule out the presence of one or more other unsaturations on the hydrocarbon chain, such as one or more other double bonds and/or one or more triple bonds, which may or may not be conjugated.

The hydrocarbon chain can optionally be interrupted by a heteroatom (for example, oxygen or sulfur) or by a functional group, insofar as the latter does not react; mention may in particular be made of a group such as especially —CO—.

The hydrocarbon chain can optionally carry one or more substituents insofar as they do not react under the reaction conditions and mention may in particular be made, as possible substituents, of a halogen atom, a nitrile group or a trifluoromethyl group.

The saturated or unsaturated and linear or branched acyclic aliphatic group can optionally carry a cyclic substituent. The term "cyclic" is understood to mean a saturated, unsaturated or aromatic carbocyclic or heterocyclic ring.

The acyclic aliphatic group can be connected to the ring via a valency bond, a heteroatom or a functional group, such as oxy, carbonyl, carboxyl, sulfonyl, and the like.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents themselves optionally carrying any substituent insofar as they do not interfere with the reactions involved in the process of the invention. Mention may in particular be made of the alkyl or alkoxy groups having from 1 to 4 carbon atoms.

The targeted aliphatic groups carrying a cyclic substituent include more particularly the aralkyl groups having from 7 to 12 carbon atoms, in particular benzyl or phenylethyl.

In the $R'^T$ group, $R^{T1}$ can also be a saturated or unsaturated carbocyclic group preferably comprising 5 or 6 carbon atoms in the ring, preferably cyclohexyl; a saturated or unsaturated heterocyclic group comprising in particular 5 or 6 atoms in the ring, including 1 or 2 heteroatoms, such as nitrogen, sulfur and oxygen atoms; a monocyclic aromatic carbocyclic group, preferably phenyl, or a condensed or noncondensed polycyclic aromatic carbocyclic group, preferably naphthyl.

With regard to $R^{T2}$ and $R^{T3}$, they are preferably a hydrogen atom or an alkyl group having from 1 to 12 carbon atoms, a phenyl group or an aralkyl group having from 7 to 12 carbon atoms, preferably a benzyl group.

In the $R'^T$ group, $R^{T1}$, $R^{T2}$ and $R^{T3}$ are more particularly a hydrogen atom or else $R^{T1}$ is a phenyl group and $R^{T2}$ and $R^{T3}$ are a hydrogen atom.

The transferable group $R^T$ can also be a group of following formula $R''^T$:

in which:

A symbolizes the residue of a ring forming all or part of a monocyclic or polycyclic, aromatic, carbocyclic and/or heterocyclic system;

$R^{T4}$, which are identical or different, are substituents on the ring, t is the number of substituents on the ring.

In particular, A is the residue of a cyclic compound which preferably has at least 4 atoms in the ring, preferably 5 or 6, which is optionally substituted and which represents at least one of the following rings:

a monocyclic aromatic carbocycle or a polycyclic aromatic carbocycle, that is to say a compound composed of at least 2 aromatic carbocycles which form, between them, ortho- or ortho- and peri-fused systems or a compound composed of at least 2 carbocycles, of which one alone of them is aromatic, which form, between them, ortho- or ortho- and peri-fused systems;

a monocyclic aromatic heterocycle comprising at least one of the heteroatoms chosen from oxygen, nitrogen and sulfur or a polycyclic aromatic heterocycle, that is to say a compound composed of at least 2 heterocycles comprising at least one heteroatom in each ring, at least one of the two rings of which is aromatic, which form, between them, ortho- or ortho- and peri-fused systems, or a compound composed of at least one carbocycle and at least one heterocycle, at least one of the rings of which is aromatic, which form, between them, ortho- or ortho- and peri-fused systems.

More particularly, the optionally substituted residue A is preferably the residue of an aromatic carbocycle, such as benzene, of an aromatic bicycle comprising two aromatic carbocycles, such as naphthalene, or of a partially aromatic bicycle comprising two carbocycles, one of the two of which is aromatic, such as 1,2,3,4-tetrahydronaphthalene.

The invention also envisages the fact that A can be the residue of a heterocycle. More particularly, the optionally substituted residue A is one of the following rings:

an aromatic heterocycle corresponding to one of the following formulae:

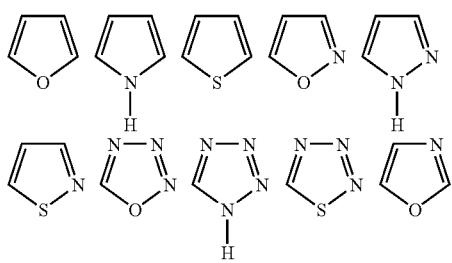

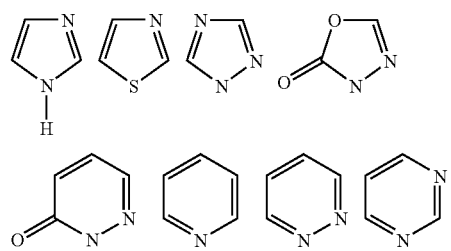

an aromatic bicycle comprising an aromatic carbocycle and an aromatic heterocycle represented by one of the following formulae:

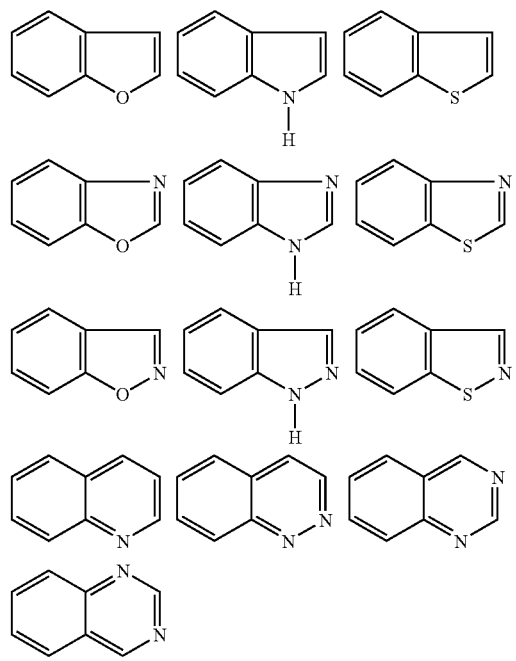

a partially aromatic bicycle comprising an aromatic carbocycle and a heterocycle represented by one of the following formulae:

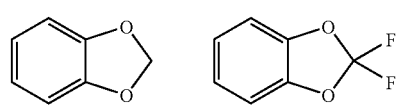

an aromatic bicycle comprising two aromatic heterocycles of formula:

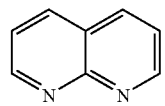

a partially aromatic bicycle comprising a carbocycle and an aromatic heterocycle corresponding to the formula:

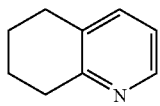

a tricycle comprising at least one carbocycle or one heterocycle which is aromatic of formulae:

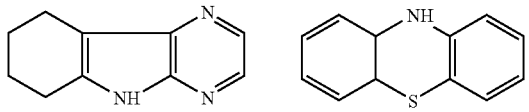

In the process of the invention, use is preferably made of a compound of formula (I) having a transferable group $R''^T$ as defined above in which A is an aromatic nucleus, preferably a benzene or naphthalene nucleus.

The transferable group $R''^T$ can carry one or more substituents. The number of substituents present on the ring depends on the carbon condensation of the ring and on the presence or absence of unsaturations in the ring. The maximum number of substituents capable of being carried by a ring is easily determined by a person skilled in the art.

In the present text, the term "several" is understood to mean generally less than 4 $R^{T4}$ substituents on an aromatic nucleus.

Examples of substituents are given below but this list does not exhibit a limiting nature.

The $R^{T4}$ group or groups, which are identical or different, are preferably one of the following groups:

a linear or branched alkyl group having from 1 to 6 carbon atoms, preferably from 1 to 4 carbon atoms, such as methyl, ethyl, propyl, isopropyl, butyl, isobutyl, sec-butyl or tert-butyl;

a linear or branched alkenyl or alkynyl group having from 2 to 6 carbon atoms, preferably from 2 to 4 carbon atoms, such as vinyl or allyl;

a linear or branched alkoxy or thioether group having from 1 to 6 carbon atoms, preferably from 1 to 4 carbon atoms, such as the methoxy, ethoxy, propoxy, isopropoxy or butoxy groups, an alkenyloxy group, preferably an allyloxy group, or a phenoxy group;

a cyclohexyl, phenyl or benzyl group;

a acyl group having from 2 to 6 carbon atoms;

a group of formula

—$R^1$—OH, —$R^1$—SH, —$R^1$—COO$R^2$, —$R^1$—CO—$R^2$, —$R^1$—CHO, —$R^1$—CN, —$R^1$—N($R^2$)$_2$, —$R^1$CO—N($R^2$)$_2$, —$R^1$—SO$_3$Z, —$R^1$—SO$_2$Z, —$R^1$—Y or —$R^1$—CF$_3$;

in which formulae $R^1$ is a valency bond or a saturated or unsaturated, linear or branched, divalent hydrocarbon group having from 1 to 6 carbon atoms, such as, for example, methylene, ethylene, propylene, isopropylene or isopropylidene; the $R^2$ groups, which are identical or different, represent a hydrogen atom, a linear or branched alkyl group having from 1 to 6 carbon atoms or a phenyl group; Z represents a hydrogen atom, an alkali metal, preferably sodium, or an $R^2$ group; and Y symbolizes a halogen atom, preferably a chlorine, bromine or fluorine atom.

It should be understood that the various substituents present in the dihalosilane of formula (I) and as just described are chosen so that they do not interfere, and in particular so that they do not react, with the reaction medium, in particular with the activating agents, under the activation conditions.

The preferred compounds of formula (I) defined above are those having the following characteristics, taken in isolation or in combination:

$X^1$ and $X^2$ are identical and are each a bromine atom or a chlorine atom, advantageously a chlorine atom;

R is chosen from the hydrogen atom, the $R^T$ radical defined below and a linear or branched alkyl radical comprising from 1 to 6 carbon atoms, preferably the methyl, ethyl, propyl, isopropyl, butyl, tert-butyl, sec-butyl, isobutyl, pentyl, neopentyl and n-hexyl radical, more preferably the methyl or ethyl radical;

$R^T$ is an optionally substituted aryl radical, for example an optionally substituted phenyl radical.

The compounds of formula (I) which are particularly preferred for the process of the present invention are those for which:

$X^1$ and $X^2$ are each a chlorine atom;

R is the methyl radical or an optionally substituted phenyl radical; and $R^T$ is an optionally substituted phenyl radical.

The compounds of formula (I) are either directly available commercially or are obtained from various silicon sources according to procedures known to a person skilled in the art or available in the scientific literature, the patent literature, computerized databases, Chemical Abstracts and the Internet.

By way of example, the compound of formula (I) defined above can be selected from chlorosilanes and in particular the compound of formula (I) can be diphenyldichlorosilane, methylphenyldichlorosilane or methyltolyldichlorosilane.

According to another aspect, the siliceous compound carrying the transferable group can advantageously be selected from silicone oils, named generically as polysiloxanes. Examples of polysiloxanes which are suitable for the process of the present invention correspond to the formula (I'):

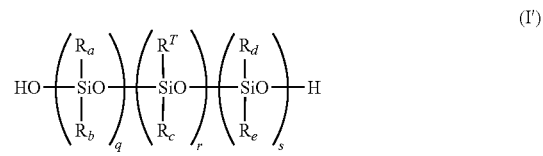

in which:

$R^T$ represents a transferable group as defined above;

$R_a$, $R_b$, $R_c$, $R_d$ and $R_e$, which are identical or different, are selected, independently of one another, from the hydrogen atom, a linear or branched alkyl radical comprising from 1 to 6 carbon atoms and the $R^T$ radical defined above;

r is an integer between 1 and 10, limits included;

q is 0 or an integer between 1 and 9, limits included; and s is 0 or an integer between 1 and 9, limits included, the sum q+r+s being between 4 and 10, limits included.

The polysiloxanes of formula (I') can also exist in the cyclic form, that is to say in the form of a ring, the endocyclic atoms of which are alternately silicon and oxygen. Such cyclic polysiloxanes can be represented diagrammatically by the following formula:

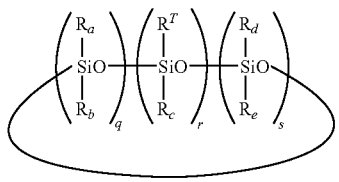

in which:

$R^T$, $R_a$, $R_b$, $R_c$, $R_d$, $R_e$, q, r and s are as defined above.

The silicone oils and in particular the cyclic or noncyclic polysiloxanes of formula (I') are known compounds which are available in particular from the silicone industries. In addition, the compounds of formula (I') can also be readily prepared by hydrolysis in a buffered aqueous medium of the compounds of formula (I) defined above.

In the same way as for the dihalosilanes of formula (I), it should be understood that the various substituents present in the silicone oils and in particular the compounds of formula (I') must be such that they do not interfere, and in particular that they do not react, with the reaction medium, in particular with the activating agents, under the activation conditions.

For the compounds of formula (I'), whether linear or cyclic, preference is given to those for which:

$R_a$, $R_b$, $R_c$, $R_d$ and $R_e$, which are identical or different, are selected, independently of one another, from the hydrogen atom, the $R^T$ radical defined below and a linear or branched alkyl radical comprising from 1 to 6 carbon atoms, preferably the methyl, ethyl, propyl, isopropyl, butyl, tert-butyl, sec-butyl, isobutyl, pentyl, neopentyl and n-hexyl radical, more preferably the methyl or ethyl radical;

$R^T$ is an optionally substituted aryl radical, for example an optionally substituted phenyl radical.

Mention may be made, among the silicone oils suitable for the process of the present invention, of those obtained by hydrolysis of the dihalosilanes of formula (I) as defined above, alkylarylpolysiloxanes, in particular methylarylpolysiloxanes, and for example the methylphenylpolysiloxane sold by Rhodia under the name of Rhodorsil H550®.

As has been said above, the siliceous compounds carrying a transferable group used in the process of the present invention must be activated before carrying out the coupling reaction proper.

The activation time depends on the nature and on the amount of the compound carrying the transferable group (for example, compound of formula (I) or of formula (I')), on the solvent used and on the activating agent used. This time generally varies from a few minutes to a few days. It may be generally less than a few hours, advantageously less than 3 hours.

When the compound carrying the transferable group is activated, it can be employed directly in the following stage b) and/or c), that is to say that there is added to it a compound carrying an acceptor group of —C═C—X type which makes possible the creation of a C—C— bond and, simultaneously or consecutively, in any order, a catalyst of palladacycle type.

More specifically, the compound carrying an acceptor group corresponds to the following formula (II):

$$R^4—X \qquad (II)$$

in which:

$R^4$ is a hydrocarbon group (acceptor group) comprising from 2 to 20 carbon atoms and has a double bond situated in the α position with respect to a leaving group X or a monocyclic or polycyclic, aromatic, carbocyclic and/or heterocyclic group; and X is a leaving group.

Preferably, $R^4$ is an aliphatic hydrocarbon group comprising a double bond in the α position with respect to the leaving group X or a cyclic hydrocarbon group comprising an unsaturation carrying the leaving group X or alternatively is a monocylic or polycyclic, aromatic, carbocyclic and/or heterocyclic group.

Preferably, X is a halogen atom, a perhaloalkyl group, such as trifluoromethyl, or a sulfonic ester group of formula —OSO$_2$—R' in which R' is a hydrocarbon group. In the formula of the sulfonic ester group, R' is a hydrocarbon group of any nature. However, given that X is a leaving group, it is advantageous from an economic viewpoint for R' to be simple in nature and consequently advantageously to be a linear or branched alkyl group having from 1 to 4 carbon atoms, preferably a methyl or ethyl group; however, R' can also be, for example, a phenyl or tolyl group or a trifluoromethyl group. For example, when the leaving group X is a triflate group, this corresponds to an —OSO$_2$—R' group in which R' represents the trifluoromethyl group.

The selection is preferably made, as preferred leaving groups, of a halogen atom, in particular a bromine or chlorine atom, more preferably a chlorine atom.

The compounds of formula (II) targeted very particularly according to the process of the invention can be categorized into two groups:

(1) those of aliphatic type carrying a double bond and which can be represented by the formula (IIa):

in which formula (IIa):

$R^{41}$, $R^{42}$ and $R^{43}$, which are identical or different, are selected, independently of one another, from the hydrogen atom and a hydrocarbon group having from 1 to 20 carbon atoms which can be a saturated or unsaturated and linear or branched aliphatic group; a saturated, unsaturated or aromatic, monocyclic or polycyclic, carbocyclic or heterocyclic group; or a sequence of aliphatic and/or carbocyclic and/or heterocyclic groups as mentioned above;

X symbolizes the leaving group as defined above, (2) those of aromatic type which are denoted subsequently by "haloaromatic compound" and which can be represented by the formula (IIb):

in which:

D symbolizes the residue of a ring forming all or part of a monocyclic or polycyclic, aromatic, carbocyclic and/or heterocyclic system, X is a leaving group as defined above, $R^{44}$, which are identical or different, are substituents on the ring, n is the number of substituents on the ring.

The invention applies to the unsaturated compounds corresponding to the formula (IIa) in which $R^{41}$ preferably represents a saturated, linear or branched, acyclic aliphatic group preferably having from 1 to 12 carbon atoms.

The invention does not rule out the presence of one or more other unsaturations on the hydrocarbon chain, such as one or more other double bonds and/or one or more triple bonds, which may or may not be conjugated.

The hydrocarbon chain can optionally be interrupted by a heteroatom (for example, oxygen or sulfur) or by a functional group, insofar as the latter does not react; mention may in particular be made of a group such as especially —CO—.

The hydrocarbon chain can optionally carry one or more substituents insofar as they do not react under the reaction conditions and mention may in particular be made, as possible substituents, of a halogen atom, a nitrile group or a trifluoromethyl group.

The saturated or unsaturated and linear or branched acyclic aliphatic group can optionally carry a cyclic substituent. The term "cyclic" is understood to mean a saturated, unsaturated or aromatic carbocyclic or heterocyclic ring.

The acyclic aliphatic group can be connected to the ring via a valency bond, a heteroatom or a functional group, such as oxy, carbonyl, carboxyl, sulfonyl, and the like.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents themselves optionally carrying any substituent insofar as they do not interfere with the reactions involved in the process of the invention. Mention may in particular be made of the alkyl or alkoxy groups having from 1 to 4 carbon atoms.

The targeted aliphatic groups carrying a cyclic substituent include more particularly the aralkyl groups having from 7 to 12 carbon atoms, in particular benzyl or phenylethyl.

In the formula (IIa), $R^{41}$ should be understood as having the same definition as that given above for $R^{71}$ and thus can also be a saturated or unsaturated carbocyclic group preferably comprising 5 or 6 carbon atoms in the ring, preferably cyclohexyl; a saturated or unsaturated heterocyclic group comprising in particular 5 or 6 atoms in the ring, including 1 or 2 heteroatoms, such as nitrogen, sulfur and oxygen atoms; a monocyclic aromatic carbocyclic group, preferably phenyl, or a condensed or noncondensed polycyclic aromatic carbocyclic group, preferably naphthyl.

With regard to $R^{42}$ and $R^{43}$, which have the definitions identical to those given for $R^{72}$ and $R^{73}$ defined above, they are preferably a hydrogen atom or an alkyl group having from 1 to 12 carbon atoms, a phenyl group or an aralkyl group having from 7 to 12 carbon atoms, preferably a benzyl group.

In the formula (IIa), $R^{41}$, $R^{42}$ and $R^{43}$ are more particularly a hydrogen atom or else $R^{41}$ is a phenyl group and $R^{42}$ and $R^{43}$ are a hydrogen atom.

Mention may in particular be made, as examples of compounds corresponding to the formula (IIa), of vinyl chloride, vinyl bromide, β-bromostyrene or β-chlorostyrene.

The invention applies in particular to the haloaromatic compounds corresponding to the formula (IIb) in which D represents the residue of a cyclic compound having the same definition as that given for the residue of the cyclic compound A of the $R''^T$ group defined above, that is to say which preferably has at least four atoms in the ring, preferably 5 or 6, which is optionally substituted and which is at least one of the rings described above for A, that is to say, a monocyclic or polycyclic aromatic carbocycle or a monocyclic aromatic heterocycle, comprising at least one of the heteroatoms selected from oxygen, nitrogen and sulfur, or a polycyclic aromatic heterocycle.

More particularly, the optionally substituted residue D is preferably the residue of an aromatic carbocycle, such as benzene, of an aromatic bicycle comprising two aromatic carbocycles, such as naphthalene, or of a partially aromatic bicycle comprising two carbocycles, one of the two of which is aromatic, such as 1,2,3,4-tetrahydronaphthalene.

The invention also envisages the fact that D can be the residue of a heterocycle. More particularly, the optionally substituted residue D is one of the rings already listed above for A of the $R''^T$ group.

In the process of the invention, use is preferably made of a haloaromatic compound of formula (IIb) in which D is an aromatic nucleus, preferably a benzene or naphthalene nucleus.

The aromatic compound of formula (IIb) can carry one or more substituents. The number of substituents present on the ring depends on the carbon condensation of the ring and on the presence or absence of unsaturations in the ring. The maximum number of substituents capable of being carried by a ring is easily determined by a person skilled in the art.

In the present text, the term "several" is understood to mean generally less than 4 $R^{44}$ substituents on an aromatic nucleus.

Examples of $R^{44}$ substituents are in particular those given as example of $R^{74}$ above in the description. However, this list of substituents does not exhibit a limiting nature.

The present invention applies very particularly to the compounds corresponding to the formula (IIb) in which the $R^{44}$ group or groups are:

a linear or branched alkyl group having from 1 to 6 carbon atoms, preferably from 1 to 4 carbon atoms, as methyl, ethyl, propyl, isopropyl, butyl, isobutyl, sec-butyl or tert-butyl;

a linear or branched alkenyl group having from 2 to 6 carbon atoms, preferably from 2 to 4 carbon atoms, such as vinyl or allyl;

a linear or branched alkoxyl group having from 1 to 6 carbon atoms, preferably from 1 to 4 carbon atoms, such as the methoxy, ethoxy, propoxy, isopropoxy or butoxy groups, an alkenyloxy group, preferably an allyloxy group, or a phenoxy group;

a group of formula —$R^1$OH, —$R^1$—N($R^2$)$_2$ or —$R^1$—SO$_3$Z, in which formulae $R^1$ is a valency bond or a saturated or unsaturated, linear or branched, divalent hydrocarbon group having from 1 to 6 carbon atoms, such as, for example, methylene, ethylene, propylene, isopropylene or isopropylidene; the $R^2$ groups, which are identical or different, represent a hydrogen atom, a linear or branched alkyl group having from 1 to 6 carbon atoms or a phenyl group; and Z represents a hydrogen atom or a sodium atom.

In the formula (IIb), n is an integer of less than or equal to 4, preferably equal to 1 or 2.

Mention may in particular be made, as examples of compounds corresponding to the formula (IIb), of p-chlorotoluene, p-bromoanisole or p-bromotrifluoromethylbenzene.

The amount of the compound carrying a leaving group of formula (II), preferably of formula (IIa) or (IIb), employed is generally expressed with respect to the amount of siliceous compound carrying a transferable group. Thus, the ratio of the number of moles of the siliceous compound carrying a transferable group to the number of moles of the compound carrying an acceptor group generally varies between 1 and 3, preferably between 1 and 2.

Before starting the coupling reaction proper, it can prove to be advantageous to add a phase transfer agent to the reaction medium. The appropriate amount of phase transfer agent depends, of course, on the nature of the various constituents of the reaction medium and is generally between 0.01 mol and 1 mol of phase transfer agent per one mole of compound carrying the acceptor group (II). This amount is preferably between 0.01 mol and 0.1 mol, advantageously approximately 0.05 mol of phase transfer agent per one mole of compound carrying the acceptor group (II).

The phase transfer agent is of any type known to a person skilled in the art. A phase transfer agent which can advantageously be used in the process of the present invention is represented by the compounds of formula:

$A^+W^-$ in which $A^+$ is a cation and $W^-$ is a counterion selected from those generally known to a person skilled in the art.

Mention may in particular be made, as counterion $W^-$, of halides, for example fluoride, chloride, bromide or iodide, or hydroxide anions, and the like.

The cation $A^+$ is generally an organic cation, in particular of onium type, especially selected from ammonium, sulfonium, phosphonium, carbenium, oxonium picolinium, pyridinium, arsonium, triazolium and iodonium cations.

Preference is particularly given, among these, to the compounds of following general formulae (III-1) and (III-2):

(III-1)

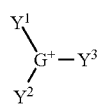

(III-2)

in which:

E is selected from the nitrogen, phosphorus or arsenic atom;

G is selected from the sulfur, oxygen, selenium and carbon atom;

$Y^1$, $Y^2$, $Y^3$ and $Y^4$, which are identical or different, are selected from:

a linear or branched alkyl radical having 1 to 16 carbon atoms which is optionally substituted by one or more phenyl, hydroxyl, halogen, nitro, alkoxy or alkoxycarbonyl groups or atoms, the alkoxy groups having 1 to 4 carbon atoms;

a linear or branched alkenyl radical having 2 to 12 carbon atoms;

an aryl radical having 6 to 10 carbon atoms which is optionally substituted by one or more alkyl groups having 1 to 4 carbon atoms, alkoxy or alkoxycarbonyl groups, the alkoxy radical having 1 to 4 carbon atoms, or halogen atoms;

it being possible for two of the said $Y^1$ to $Y^4$ radicals together to form a linear or branched alkylene, alkenylene or alkadienylene radical having from 3 to 6 carbon atoms.

Quaternary ammonium derivatives are particularly advantageous, in particular tetraalkylammoniums, trialkylbenzylammoniums, dialkyldiphenylammoniums and alkyltriphenylammoniums.

Mention may be made, among the compounds of formula $A^+W^-$, of the following compounds: tetrabutylammonium iodide, tetrabutylammonium chloride, tetrabutylammonium bromide, tetramethylammonium bromide, cetyltrimethylammonium bromide, $Bu_4NSCN$, $Bu_4NOCN$, $Bu_4NCN$, $Et_4NCN$, $KCN$, $Bu_4NOSO_2NH_2$, $Bu_4NONO_2$, $Bu_4NONO$, $Bu_4NSPh$, $Et_4NSH$, $MeSNa$, $Bu_4NSEt$, $NaSO_2Me$, $Bu_4NOAc$, $Bu_4NOMe$, $Bu_4NHSO_4$, $Bu_4NN_3$, $CF_3SCu$ and $(Me_2N)_3SOCF$.

Mention may in particular be made, among the phase transfer agents which are particularly preferred for the process of the present invention, of tetrabutylammonium iodide, tetrabutylammonium chloride, tetrabutylammonium bromide, tetramethylammonium bromide and cetyltrimethylammonium bromide.

It remains, of course, that the presence of a phase transfer agent is not essential for the process of the invention.

Thus, the coupling reaction, optionally in the presence of a phase transfer agent as just defined, is carried out at a temperature generally between ambient temperature and 150° C., preferably between 50° C. and 110° C., for a period of time of usually between a few minutes and 4 hours, generally in the region of 15 minutes to 1 hour 30 minutes.

Depending on the nature of the compound of formula (II), the coupling reaction can even be virtually instantaneous, indeed even instantaneous, or alternatively can last for more than 1 hour 30 minutes, indeed even more than 4 hours.

The solvent of the coupling reaction proper (stage b)) is generally identical to that used in the stage of activation of the halosilyl compound (stage a)). This is generally the case when the reaction product from stage a) is not isolated and is charged directly to stage b).

However, it can prove to be useful to add solvent before charging, to stage b), the reaction product from stage a), whether or not the latter has been isolated. The solvent of stage b) will advantageously be selected from the possible solvents defined for stage a) and as described above.

Generally, the amount of solvent used in the coupling stage is such that the concentration of the compound comprising an acceptor group of formula (II) is between 0.01M and 2M, preferably between 0.1M and 1M.

The coupling stage b) is additionally characterized by the addition (stage c)) of a catalyst of palladacycle type, before, during or even after the addition of the compound carrying an acceptor group of formula (II) as defined above.

The term "catalyst of palladacycle type" (called simply "palladacycle" in the continuation of the present account) is understood to mean a cyclic compound comprising a carbon-palladium bond in the ring. This carbon-palladium bond generally results from a carbopalladation reaction, in particular substitution, by a palladium atom, of a hydrogen atom carried by a carbon atom of $sp^2$ hybridization, for example an aromatic carbon atom, or by a carbon atom of $sp^3$ hybridization.

Such palladacycles are well known in the prior art and have been described, for example, by K. Hiraki et al. (*Inorg. Synth.*, 1989, 26, 208-210), M. Pfeffer (*Inorg. Synth.*, 1989, 26, 211-214), C. Nájera et al. (*J. Org. Chem.*, 2002, 67, 5588-5594), R. B. Bedford et al. (*Angew. Chem. Int. Ed.*, 2002, 41(21), 4120-4122) and J. Dupont et al. (*Eur. J. Inorg. Chem.*, 2001, 1917-1927).

By way of example, the palladacycles which can in particular be used in the process of the present invention correspond to the following formula (IV):

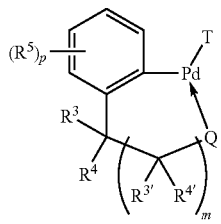

(IV)

in which:

Q is a group of formula (Q-1) or a group of formula (Q-2):

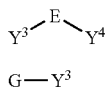

(Q-1)

G—Y³ (Q-2)

in which groups:

E is selected from the nitrogen, phosphorus or arsenic atom;

G is selected from the sulfur, oxygen, selenium and carbon atom; and $Y^3$ and $Y^4$, which are identical or different, are selected from:
- a linear or branched alkyl radical having 1 to 16 carbon atoms which is optionally substituted by one or more phenyl, hydroxyl, halogen, nitro, alkoxy or alkoxycarbonyl groups or atoms, the alkoxy groups having 1 to 4 carbon atoms;
- a linear or branched alkenyl radical having 2 to 12 carbon atoms;
- an aryl radical having 6 to 10 carbon atoms which is optionally substituted by one or more alkyl groups having 1 to 4 carbon atoms, alkoxy or alkoxycarbonyl groups, the alkoxy radical having 1 to 4 carbon atoms, or halogen atoms;
- it being possible for $Y^3$ to $Y^4$ together to form a linear or branched alkylene, alkenylene or alkadienylene radical having from 3 to 6 carbon atoms;
- it being possible for $Y^3$ or $Y^4$ to form, with $R^4$ or $R^{4'}$ and with the atoms to which they are connected, an unsaturated or completely or partially unsaturated 5- or 6-membered ring;
- it additionally being possible for one of $Y^3$ or $Y^4$ to be hydrogen, the other being as defined above;

it additionally being possible for $Y^3$ to form a bond with $R^3$ (or $R^{3'}$) when E is the nitrogen atom and, in this case, $Y^4$ can also be the hydroxyl group;

T is a counterion commonly understood as such by a person skilled in the art and is generally selected from the anions of the following groups: —F, —Cl, —Br, —I, —CN, —OCN, —SCN, —CF₃, —OCF₃, —SCF₃, —ONO, —ONO₂, —OSO₂N(R⁶) (R⁷), —SO₂R⁸, —OSO₂R⁸, —O(O)CR⁸, —SR⁸, —N₃ and —OR⁸;

$R^3$, $R^4$, $R^{3'}$ and $R^{4'}$, which are identical or different, are selected from the hydrogen atom and a linear or branched alkyl radical comprising from 1 to 6 carbon atoms; preferably, $R^3$, $R^4$, $R^{3'}$ and $R^{4'}$, which are identical or different, are the hydrogen atom or the methyl radical, more preferably the hydrogen atom; it additionally being possible for $R^3$, $R^4$, $R^{3'}$ or $R^{4'}$ to form, with $Y^3$ and/or $Y^4$ and/or $R^5$, together with the atoms to which they are connected, an unsaturated or completely or partially unsaturated 5- or 6-membered ring;

$R^5$, which are identical or different, are substituents on the ring, preferably one of the groups selected from the linear or branched alkyl group having from 1 to 6 carbon atoms, preferably from 1 to 4 carbon atoms, such as methyl, ethyl, propyl, isopropyl, butyl, isobutyl, sec-butyl or tert-butyl; a linear or branched alkenyl or alkynyl group having from 2 to 6 carbon atoms, preferably from 2 to 4 carbon atoms, such as vinyl or allyl; a linear or branched alkoxy or thioether group having from 1 to 6 carbon atoms, preferably from 1 to 4 carbon atoms, such as the methoxy, ethoxy, propoxy, isopropoxy or butoxy groups, an alkenyloxy group, preferably an allyloxy group, or a phenoxy group; a cyclohexyl, phenyl or benzyl group; an acyl group having from 2 to 6 carbon atoms; a group of formula —R¹—OH, —R¹—SH, —R¹—COOR², —R¹—CO—R², —R¹—CHO, —R¹—CN, —R¹—N(R²)₂, —R¹—CO—N(R²)₂, —R¹—SO₃Z, —R¹—SO₂Z, —R¹—Y or —R¹—CF₃; in which formulae $R^1$ is a valency bond or a saturated or unsaturated, linear or branched, divalent hydrocarbon group having from 1 to 6 carbon atoms, such as, for example, methylene, ethylene, propylene, isopropylene or isopropylidene; the $R^2$ groups, which are identical or different, are a hydrogen atom or a linear or branched alkyl group having from 1 to 6 carbon atoms or a phenyl group; Z is a hydrogen atom, an alkali metal, preferably sodium, or an $R^2$ group; Y symbolizes a halogen atom, preferably a chlorine, bromine, iodine or fluorine atom; $R^5$ can additionally form, with $R^3$, $R^4$, $R^{3'}$ or $R^{4'}$, $Y^3$, $Y^4$ or another $R^5$ substituent, together with the atoms to which they are connected, an unsaturated or completely or partially unsaturated 5- or 6-membered ring;

$R^6$ and $R^7$, which are identical or different, are the hydrogen atom or a linear or branched $C_1$-$C_{16}$ alkyl group;

$R^8$ is a linear or branched $C_1$-$C_{16}$ alkyl group;

p is the number of substituents on the ring, that is to say 0, 1, 2, 3 or 4; and m is 0 or 1.

The palladacycle of formula (IV) can also exist in the dimeric form.

Preference is given, among the palladacycles of formula (IV) defined above, to those having one or more of the following characteristics, taken in isolation or in combination:

Q is a group of formula (Q-1):

in which:

E is the nitrogen atom;

$Y^3$ and $Y^4$, which are identical or different, are a linear or branched alkyl radical having 1 to 16 carbon atoms, preferably from 1 to 6 carbon atoms, more preferably the methyl radical; it additionally being possible for one of $Y^3$ or $Y^4$ to be hydrogen, the other being as defined above;

it additionally being possible for $Y^3$ to form a bond with $R^3$ (or $R^{3'}$) when E is the nitrogen atom and, in this case, $Y^4$ can also be the hydroxyl group;

T is a halogen, preferably —F, —Cl, —Br or —I, more preferably —Cl, or else the triflate group or the acetate group;

$R^3$, $R^4$, $R^{3'}$ and $R^{4'}$, which are identical or different, are the hydrogen atom or the methyl radical, more preferably the hydrogen atom;

$R^5$, which are identical or different, are one of the groups selected from a linear or branched alkyl group having from 1 to 6 carbon atoms, preferably from 1 to 4 carbon atoms, such as methyl, ethyl, propyl, isopropyl, butyl, isobutyl, sec-butyl or tert-butyl; or a halogen atom, preferably a chlorine, bromine or fluorine atom;

p is 0, 1 or 2; and m is 0.

An altogether preferred example of palladacycle of formula (IV) is a palladacycle, in the dimeric form, of following formula (IV-1):

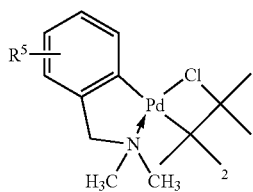

(IV-1)

in which $R^5$ is as defined above.

Preference is additionally given, among the compounds of formula (IV-1) above, to those for which $R^5$ is hydrogen or a halogen atom, for example fluorine or chlorine.

Palladacycles, in the dimeric form, which are particularly preferred are the following palladacycles P1 and P2:

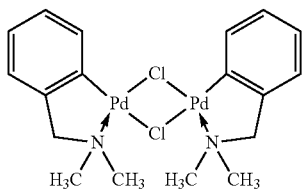

(P1)

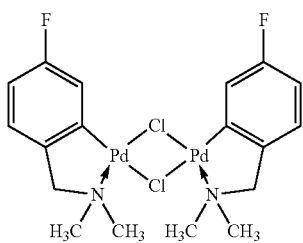

(P2)

Of course, any other palladacycle, such as those presented in the disclosures of the prior art, for example the papers cited above, may be suitable for the process of the present invention.

Solely by way of illustration, some examples of such palladacycles of the prior art which can be used in the process of the present invention, even if they do not correspond to the formula (IV) defined above, are as follows:

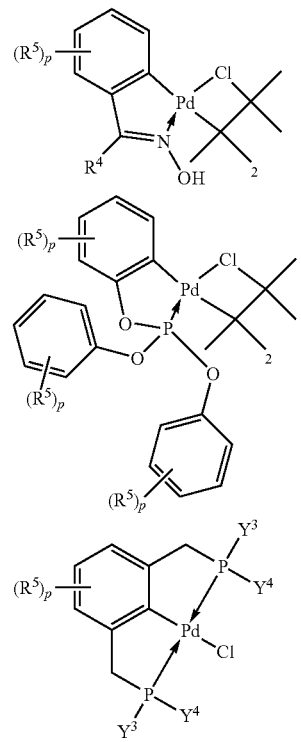

where $R^4$, $R^5$, $Y^3$, $Y^4$ and p can, for example, take the values defined for the above formula (IV).

The catalysts of palladacycle type used in the process of the present invention are in the liquid or solid form. In the latter case, the catalyst can be introduced directly into the reactant or after dilution in an appropriate solvent, for example the solvent used in stages a) or b) and as defined above.

The process of the present invention, involving catalysts of palladacycle type with silyl derivatives, shows that the reaction product is virtually devoid of homocoupling product, without it being necessary to have recourse to the addition of phosphines. In addition, the yields observed are substantially better than those obtained with the coupling processes described to date in the prior art and the reaction times are generally shorten than those known in the prior art.

Another very advantageous characteristic of the process of the invention is the very low amount of catalyst necessary to give very good results, both qualitatively and quantitatively. Specifically, the amounts of catalyst employed in the process of the present invention are generally between 0.0005 mol % and 2 mol %, preferably between 0.01 mol % and 1 mol %, with respect to the compound carrying the acceptor group of formula (II). In particular, the process of the invention has been shown to be entirely suitable and effective with amounts of catalysts of less than 0.1 mol % (1000 ppm), with respect to the compound carrying the acceptor group of formula (II).

In the account of the process according to the invention which has just been described, the compounds of formulae (I), (I'), (II), (III) and (IV) are either directly available commercially or are easily prepared according to conventional procedures known to a person skilled in the art, procedures available, for example, in the scientific literature, in patents and patent applications, in the abstracts of Chemical Abstracts and via the Internet.

On conclusion of the coupling reaction, the reaction product is separated from the reaction medium, isolated and purified according to techniques known to a person skilled in the art or according to known procedures readily accessible from in particular the sources cited above.

The reaction product from the process according to the invention is a compound which can be represented diagrammatically by the following formula (V), when it is obtained by coupling a compound carrying a transferable group and a compound carrying an acceptor group as are defined above:

$$R^T—R^A \qquad (V)$$

in which compound $R^T$ and $R^A$ are as defined above.

The compounds (V) have entirely advantageous applications in a great many fields, such as, for example, those of agrochemistry, pharmaceuticals, electronics and high performance products used, for example, in the preparation of liquid crystals, and the like.

The purpose of the following examples is to illustrate the process of the present invention, without, however, introducing any limitation thereto.

EXAMPLES

Synthesis of the Catalyst P1

Palladium chloride ($PdCl_2$, 1.26 g), lithium chloride (LiCl, 0.6 g) and 30 ml of water are charged to a reactor. The stirred mixture is brought to boiling point for 1 hour 30. The water is evaporated under reduced pressure and the solid obtained is taken up in 10 ml of methanol. The solvent is evaporated under reduced pressure and the brown solid is dissolved in 35 g of methanol, and then N,N-dimethylbenzylamine (1.06 g) is added.

The mixture is stirred for 5 minutes and then triethylamine (0.7 g) is added dropwise over 1 hour. At the end of the addition, stirring is maintained for 8 hours. The yellow precipitate obtained is filtered off and washed three times with methanol and twice with ether. The yellow solid is dried under reduced pressure. 1.78 g of palladacycle P1 are obtained (Yield: 91.2%).

The synthesis of the palladacycle P2 defined above in the description is also carried out according to a similar procedure.

Examples of Coupling Operations Starting from Diphenyldichlorosilane $Ph_2SiCl_2$ 20 ml of dioxane and 80 mmol of sodium hydroxide, reduced to powder, followed by 20 mmol of diphenyldichlorosilane ($Ph_2SiCl_2$), are introduced into a reactor. The stirred mixture is heated at 100° C. for 30 minutes. Tetrabutylammonium bromide (0.5 mmol), 4-trifluoromethyl-1-bromobenzene (10 mmol) and the palladacycle P2 (0.005 mmol) are then charged at 70° C.

The mixture is stirred at 100° C. for 30 minutes, then cooled to 40° C. and hydrolyzed with 20 ml of water. The reaction mass is extracted with 2×20 ml of toluene. After evaporating the solvents from the combined organic phases, 9.5 mmol of the expected product, [4'-(trifluoromethyl)phenyl]benzene, are obtained (Yield 95%).

Examples of Coupling Operations Starting from Methylphenyldichlorosilane ($PhMeSiCl_2$)

20 ml of anisole and 80 mmol of sodium hydroxide, reduced to powder, are introduced into a reactor. 20 mmol of methylphenyldichlorosilane are subsequently run in, over 30 minutes, onto the stirred mixture heated to 85° C. After keeping stirred at 85° C. for 1 hour, tetrabutylammonium bromide (0.5 mmol), the aryl bromide (10 mmol) and the P1 catalyst (0.005 mmol) are introduced.

The mixture is stirred at 110° C. for 1 hour 30 minutes and then cooled to 40° C. before hydrolysis with 20 ml of water. The organic phase is separated from the reaction medium and quantitatively determined by GC (gas chromatography) with internal calibration. The yields (RY) of biphenyls (V) corresponding to the starting aryl bromide (II) obtained are given in the following table:

-continued

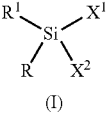

| | | | | RY (% by weight) |
|---|---|---|---|---|
| (I) | (II) | | (V) | |
| 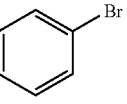 |  | |  | 96.8 |

Examples of Coupling Operations Starting from Methylphenylpolysiloxane 20 ml of anisole and 40 mmol of sodium hydroxide, reduced to fine powder, are introduced into a reactor. 20 mmol (expressed as Si unit) of methylphenylpolysiloxane silicone oil, sold by Rhodia under the name Rhodorsil H550®, are subsequently run in, over 10 minutes, onto the stirred mixture heated to 85° C. After keeping stirred at 85° C. for one hour, the P1 catalyst (0.005 mmol) and the aryl bromide (10 mmol) are introduced.

The mixture is stirred and heated at 110° C. for 1 hour 30 minutes and then cooled to 40° C. before hydrolysis with 20 ml of water. The organic phase is separated by settling and the aqueous phase is extracted with 20 ml of anisole. The organic extracts are combined and quantitatively determined by GC (gas chromatography) with internal calibration. Complete conversion is obtained and the yields (RY %) obtained are as follows:

in which the siliceous compound carrying a transferable group is a dihalosilane of formula (I):

$$\begin{array}{c} R^T \diagdown \diagup X^1 \\ Si \\ R \diagup \diagdown X^2 \end{array} \quad (I)$$

where:

$X^1$ and $X^2$, which are identical or different, are, independently of one another, a halogen atom selected from fluorine, chlorine, bromine and iodine;

$R^T$ is the transferable group and is selected from an aryl, vinyl and allyl radical, wherein said radical may optionally be substituted; and

| Silicone oil | $R^A$—X | $R^T$—$R^A$ | RY (% by weight) |
|---|---|---|---|
| Rhodorsil H550 ® | 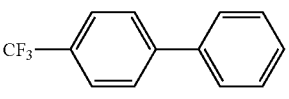 |  | 98 |
| Rhodorsil H550 ® | 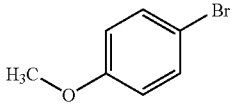 | 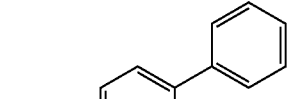 | 99 |

What is claimed is:

1. A process for creating a carbon-carbon bond by coupling a transferable group to an acceptor group comprising the steps of:
   a) activating a siliceous compound comprising a group which can be transferred by an activating agent;
   b) adding a derivative carrying an acceptor group and, simultaneously or consecutively, in any order; and
   c) adding a compound of palladacycle type which acts as a catalyst of the reaction of coupling the transferable group to the acceptor group by creation of said carbon-carbon bond, R is selected from the hydrogen atom, the $R^T$ radical defined above, and a linear or branched alkyl radical comprising from 1 to 6 carbon atoms;

wherein said process is performed without the use of a phosphine.

2. The process as claimed in claim 1, in which the activating agent is an anionic nucleophilic compound selected from hydroxides of alkali metals and alkaline earth metals, alkoxides, carbonates, and amides.

3. The process as claimed in claim 2, in which the activating agent is selected from sodium hydroxide, lithium hydroxide, potassium hydroxide, barium hydroxide, barium oxide and the potassium salt of hexamethyldisilazane.

4. The process as claimed in claim 1, in which step a) is carried out in a medium comprising a polar solvent.

5. The process as claimed in claim 4, in which the polar solvent in step a) is selected from dioxane, tetrahydrofuran, anisole, dibutyl ether, methyl tert-butyl ether, ethylene glycol diethyl ether, diethylene glycol diethyl ether and diisopropyl ether.

6. The process as claimed in claim 1, further comprising the step:
d) separating and isolating the product of the coupling reaction.

7. The process as claimed in claim 1, in which the dihalosilane of formula (I) has the following characteristics, taken in isolation or in combination:
$X^1$ and $X^2$ are identical and are each a bromine atom or a chlorine atom;
R is chosen from the hydrogen atom, the $R^T$ radical defined below and a linear or branched alkyl radical comprising from 1 to 6 carbon atoms; and
$R^T$ is an optionally substituted phenyl radical.

8. The process as claimed in claim 7, in which the dihalosilane of formula (I) is a chlorosilane.

9. The process as claimed in claim 8, in which the dihalosilane of formula (I) is diphenyldichlorosilane, methylphenyldichlorosilane or methyltolyldichlorosilane.

10. A process for creating a carbon-carbon bond by coupling a transferable group to an acceptor group comprising the steps of:
a) activating a siliceous compound carrying a group which can be transferred by an activating agent;
b) adding a derivative carrying an acceptor group and, simultaneously or consecutively, in any order, and
c) adding a compound of palladacycle type which acts as catalyst of the reaction of coupling the transferable group to the acceptor group by creation of said carbon-carbon bond,
in which the siliceous compound carrying a transferable group is a silicone oils;
wherein said process is performed without the use of a phosphine.

11. The process as claimed in claim 10, in which the silicone oil is a polysiloxane of formula (I'):

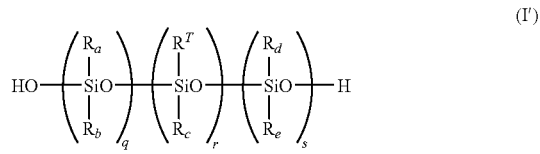

in which:
$R^T$, a transferable group, is an optionally substituted phenyl radical;
$R_a$, $R_b$, $R_c$, $R_d$ and $R_e$, which are identical or different, are selected, independently of one another, from the hydrogen atom, a linear or branched alkyl radical comprising from 1 to 6 carbon atoms and the $R^T$ radical defined above;
r is an integer from 1 and 10;
q is 0 or an integer from 1 and 9; and
s is 0 or an integer from 1 and 9,
the sum q+r+s being from 4 and 10.

12. The process as claimed in claim 11, in which the polysiloxane is in the cyclic form:

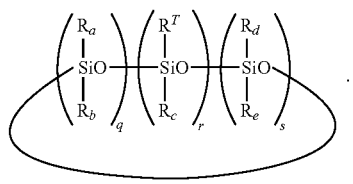

13. The process as claimed in claim 1, in which the compound carrying an acceptor group corresponds to the formula (II):

$$R^A—X \qquad (II)$$

in which:
$R^A$ is a hydrocarbon group (acceptor group) comprising from 2 to 20 carbon atoms and has a double bond situated in the α position with respect to a leaving group X or a monocyclic or polycyclic, aromatic, carbocyclic and/or heterocyclic group; and
X is a leaving group, selected from the group consisting of a halogen atom, a perhaloalkyl group, and a sulfonic ester group of formula —OSO$_2$—R', in which R' is a hydrocarbon group.

14. The process as claimed in claim 1, in which the compound carrying an acceptor group corresponds to the formula (IIa):

in which:
$R^{A1}$, $R^{A2}$ and $R^{A3}$, which are identical or different, are selected, independently of one another, from a hydrogen and a hydrocarbon group having from 1 to 20 carbon atoms which can be a saturated or unsaturated and linear or branched aliphatic group; a saturated, unsaturated or aromatic, monocyclic or polycyclic, carbocyclic or heterocyclic group; or a sequence of aliphatic and/or carbocyclic and/or heterocyclic groups; and
X symbolizes a leaving group selected from the group consisting of a halogen atom, a perhaloalkyl group, and a sulfonic ester group of formula —OSO$_2$—R', in which R' is a hydrocarbon group.

15. The process as claimed in claim 14, in which the compound carrying an acceptor group is selected from vinyl chloride, vinyl bromide, β-bromostyrene and β-chlorostyrene.

16. The process as claimed in claim 1, in which the compound carrying an acceptor group corresponds to the formula (IIb):

in which:

D symbolizes the residue of a ring forming all or part of a monocyclic or polycyclic, aromatic, carbocyclic and/or heterocyclic system, X is a leaving group selected from a bromine atom or a chlorine atom, $R^{44}$, which are identical or different, are substituents on the ring, and n is the number of substituents on the ring.

17. The process as claimed in claim 16, in which the compound carrying an acceptor group corresponds to the formula (IIb) where D is the residue of a cyclic compound which is optionally substituted and which represents at least one of the following rings:

a monocyclic aromatic carbocycle or a polycyclic aromatic carbocycle comprising at least 2 aromatic carbocycles which form, between them, ortho- or ortho- and pen-fused systems or a compound composed of at least 2 carbocycles, of which one of said carbocycles is aromatic, and the at least 2 carbocycles form, between them, ortho- or ortho- and pen-fused systems;

a monocyclic aromatic heterocycle comprising at least one heteroatom selected from oxygen, nitrogen and sulfur, or a polycyclic aromatic heterocycle comprising at least 2 heterocycles comprising at least one heteroatom in each ring, wherein at least one of the two rings of which is aromatic, which form, between them, ortho- or ortho- and pen-fused systems, or a compound comprising at least one carbocycle and at least one heterocycle, wherein at least one of the rings is aromatic, and said at least one carbocycle and at least one heterocycle form between them, ortho- or ortho- and pen-fused systems.

18. The process as claimed in claim 17, in which the compound carrying an acceptor group corresponds to the formula (IIb) where D is the residue of an optionally substituted aromatic carbocycle, an aromatic bicycle comprising two aromatic carbocycles, or of a partially aromatic bicycle comprising two carbocycles, one of the two of which is aromatic.

19. The process as claimed in claim 17, in which the compound carrying an acceptor group corresponds to the formula (IIb) where D is the residue of a heterocycle selected from the group consisting of:

an aromatic heterocycle selected from the group consisting of:

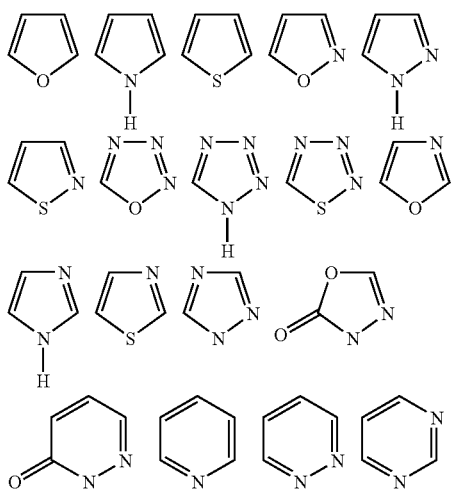

an aromatic bicycle comprising an aromatic carbocycle and an aromatic heterocycle, said aromatic bicycle selected from the group consisting of:

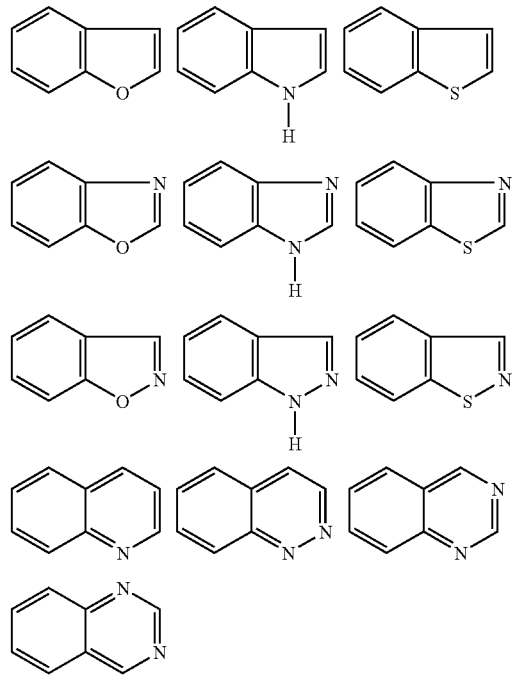

a partially aromatic bicycle comprising an aromatic carbocycle and a heterocycle, said partially aromatic bicycle selected from the group consisting of:

an aromatic bicycle comprising two aromatic heterocycles:

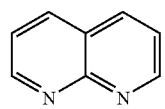

a partially aromatic bicycle comprising a carbocycle and an aromatic heterocycle:

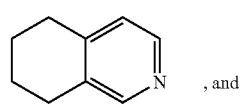, and a tricycle comprising at least one carbocycle or one heterocycle which is aromatic, said tricycle selected from the group consisting of:

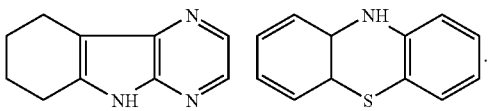

20. The process as claimed in claim 1, in which the compound carrying an acceptor group is selected from p-chlorotoluene, p-bromoanisole and p-bromotrifluoro-methylbenzene.

21. The process as claimed in claim 1, in which the palladacycle compound corresponds to formula (IV):

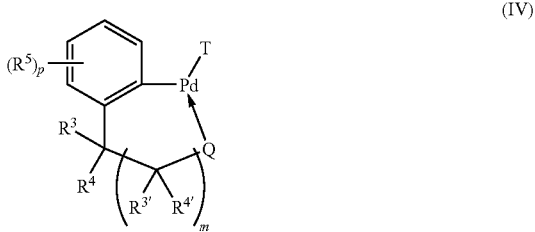

in which:

Q is a group of formula (Q-1) or a group of formula (Q-2):

in which groups:

E is selected from a nitrogen, phosphorus and arsenic atom;

G is selected from a sulfur, oxygen, selenium and carbon atom; and $Y^3$ and $Y^4$, which are identical or different, are selected from:

a linear or branched alkyl radical having 1 to 16 carbon atoms which is optionally substituted by one or more phenyl, hydroxyl, halogen, nitro, alkoxy or alkoxycarbonyl groups or atoms, the alkoxy groups having 1 to 4 carbon atoms;

a linear or branched alkenyl radical having 2 to 12 carbon atoms;

an aryl radical having 6 to 10 carbon atoms which is optionally substituted by one or more alkyl groups having 1 to 4 carbon atoms, alkoxy or alkoxycarbonyl groups, the alkoxy radical having 1 to 4 carbon atoms, or halogen atoms;

additionally form, with $R^3$, $R^4$, $R^{3'}$ or $R^{4'}$, $Y^3$, $Y^4$ or another $R^5$ substituent, together with the atoms to which they are connected, an unsaturated or completely or partially saturated 5- or 6-membered ring;

$R^6$ and $R^7$, which are identical or different, are the hydrogen atom or a linear or branched $C_1$-$C_{16}$ alkyl group;

$R^8$ is a linear or branched $C_1$-$C_{16}$ alkyl group;

p is the number of substituents on the ring, and has a value of 0, 1, 2, 3 or 4; and m is 0 or 1, wherein the palladacycle of formula (IV) can be present in the dimeric form.

22. The process as claimed in claim 21, in which the palladacycle of formula (IV) has one or more of the following characteristics, taken in isolation or in combination:

Q is a group of formula (Q-1):

in which:

E is the nitrogen atom;

$Y^3$ and $Y^4$, which are identical or different, are a linear or branched alkyl radical having 1 to 16 carbon atoms, or one of $Y^3$ or $Y^4$ is hydrogen, with the other being as defined above;

it additionally being possible for $Y^3$ to form a bond with $R^3$ (or $R^{3'}$) when E is the nitrogen atom and, in this case, $Y^4$ can also be the hydroxyl group;

T is a halogen, a triflate or acetate group;

$R^3$, $R^4$, $R^{3'}$ and $R^{4'}$, which are identical different, are the hydrogen atom or the methyl radical;

$R^5$, which are identical or different, are one of the groups selected from a linear or branched alkyl group having from 1 to 6 carbon atoms, or a halogen atom;

it being possible for $Y^3$ to $Y^4$ together to form a linear or branched alkylene, alkenylene or alkadienylene radical having from 3 to 6 carbon atoms;

it being possible for $Y^3$ or $Y^4$ to form, with $R^4$ or $R^{4'}$ and with the atoms to which they are connected, an unsaturated or completely or partially unsaturated 5- or 6-membered ring;

it additionally being possible for one of $Y^3$ or $Y^4$ to be hydrogen, and the other being as defined above;

it additionally being possible for $Y^3$ to form a bond with $R^3$ (or $R^{3'}$) when E is the nitrogen atom, $Y^4$ can also be a hydroxyl group;

T is a counterion selected from anions of the following groups: —F, —Cl, —Br, —I, —CN, —OCN, —SCN, —CF$_3$, —OCF$_3$, —SCF$_3$, —ONO, —ONO$_2$, —OSO$_2$N(R$_6$)(R$_7$), —SO$_2$R$_8$, —OSO2R$_8$, —O(O)CR$_8$, —SR$_8$, —N$_3$ and —OR$_8$;

$R^3$, $R^4$, $R^{3'}$ and $R^{4'}$, which are identical or different, are selected from the hydrogen atom and a linear or branched alkyl radical comprising from 1 to 6 carbon atoms; preferably, $R^3$, $R^4$, $R^{3'}$ and $R^{4'}$, which are identical or different, are the hydrogen atom or the methyl radical, more preferably the hydrogen atom; it additionally being possible for $R^3$, $R^4$, $R^{3'}$ or $R^{4'}$ to form, with $Y^3$ and/or $Y^4$ and/or $R^5$, together with the atoms to which they are connected, an unsaturated or completely or partially saturated 5- or 6-membered ring;

$R^5$ a group selected from the linear or branched alkyl group having from 1 to 6 carbon atoms; a linear or branched alkenyl or alkynyl group having from 2 to 6 carbon atoms; a linear or branched alkoxy or alkylthio group having from 1 to 6 carbon atoms; an alkenyloxy group; a cyclohexyl, phenyl or benzyl group; an acyl group having from 2 to 6 carbon atoms; a group of formula —R$^1$—OH, —R$^1$—SH, —R$^1$—COOR$^2$, —R$^1$—CO—R$^2$, —R$^1$—CHO, —R$^1$—CN, —R$^1$—N(R$^2$)$_2$, —R$^1$—CO—N(R$^2$)$_2$, —R$^1$—SO$_3$Z, —R$^1$—SO$_2$Z, —R$^1$—Y or —R$^1$—CF$_3$; in which formulae R$^1$ is a valency bond or a saturated or unsaturated, linear or branched, divalent hydrocarbon group having from 1 to 6 carbon atoms; the $R^2$ groups, which are identical or different, are a hydrogen atom or a linear or branched alkyl group having from 1 to 6 carbon atoms or a phenyl group; Z is a hydrogen atom, an alkali metal, or an $R^2$ group; Y symbolizes a halogen atom; $R^5$ can p is 0, 1 or 2; and m is 0.

23. The process as claimed in claim 21, in which the palladacycle corresponds to the following formula (IV-1):

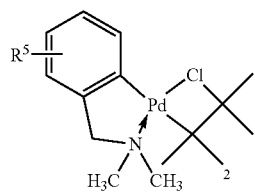

(IV-1)

in which $R^5$, which are identical or different, are selected from the group consisting of hydrogen, a linear or branched alkyl group having from 1 to 6 carbon atoms, and a halogen atom.

24. The process as claimed in claim 23, in which the palladacycle is selected from the palladacycle P1 and the palladacycle P2:

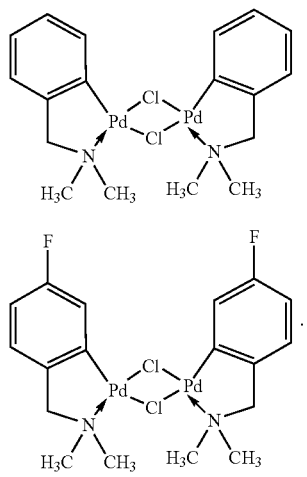

(P1)

(P2)

25. The process as claimed in claim 1, in which the amount of catalyst employed is generally between 0.0005 mol % and 2 mol %, with respect to the compound carrying the acceptor group.

26. The process as claimed in claim 5, in which the solvent in step a) is dioxane or anisole.

27. The process as claimed in claim 1, further comprising, between step b) and step c), the step of adding a phase transfer agent.

28. The process as claimed in claim 27, in which the phase transfer agent is selected from tetrabutylammonium iodide, tetrabutylammonium chloride, tetrabutylammonium bromide, tetramethylammonium bromide and cetyltrimethylammonium bromide.

29. The process as claimed in claim 6, comprising the steps of:

a) activating a dichlorosilane by an alkali metal or alkaline earth metal hydroxide;

b) adding an aryl halide;

c) adding a palladacycle catalyst, optionally in the presence of a phase transfer agent; and d) separating and isolating the product of the coupling reaction.

30. The process as claimed in claim 29, comprising the steps of:

a) activating diphenyldichlorosilane by sodium hydroxide;

b) adding 4-trifluoromethyl-1-bromobenzene;

c) adding palladacycle catalyst P2, in the presence of tetrabutylammonium bromide as phase transfer agent; and d) separating and isolating the product of the coupling reaction, which is [4'-(trifluoromethyl)phenyl]benzene.

31. The process as claimed in claim 29, comprising the steps of:

a) activating methylphenyldichlorosilane by sodium hydroxide;

b) adding 4-trifluoromethyl-1-bromobenzene;

c) adding palladacycle catalyst P1, in the presence of tetrabutylammonium bromide as phase transfer agent; and d) separating and isolating the product of the coupling reaction, which is [4'-(trifluoromethyl)phenyl]benzene.

32. The process as claimed in claim 29, comprising the steps of:

a) activating methylphenyldichlorosilane by sodium hydroxide;

b) adding 2-methyl-1-bromobenzene;

c) adding palladacycle catalyst P1, in the presence of tetrabutylammonium bromide as phase transfer agent; and d) separating and isolating the product of the coupling reaction, which is (2'-methylphenyl)benzene.

33. The process as claimed in claim 29, comprising the steps of:

a) activating methylphenyldichlorosilane by sodium hydroxide;

b) adding 4-methoxy-1-bromobenzene;

c) adding palladacycle catalyst P1, in the presence of tetrabutylammonium bromide as phase transfer agent; and d) separating and isolating the product of the coupling reaction, which is (4'-methoxyphenyl)benzene.

34. The process as claimed in claim 6, wherein steps a, b and c comprise:

a) activating a silicone oil by an alkali metal or alkaline earth metal hydroxide;

b) adding an aryl halide; and c) adding a palladacycle catalyst, optionally in the presence of a phase transfer agent.

35. The process as claimed in claim 34, comprising the steps of:

a) activating methylphenylpolysiloxane by sodium hydroxide;

b) adding 4-trifluoromethyl-1-bromobenzene;

c) adding palladacycle catalyst P1; and d) separating and isolating the product of the coupling reaction, which is [4'-(trifluoromethyl)phenyl]benzene.

36. The process as claimed in claim 34, comprising the steps of:

a) activating methylphenylpolysiloxane by sodium hydroxide;

b) adding 4-methoxy-1-bromobenzene;

c) adding palladacycle catalyst P1; and d) separating and isolating the product of the coupling reaction, which is (4'-methoxyphenyl)benzene.

37. The process as claimed in claim 18, in which the compound carrying an acceptor group corresponds to the formula (IIb) where D is selected from benzene, naphthalene, or 1,2,3,4-tetrahydronaphthalene.

38. The process as claimed in claim 7, where R in formula (I) is a linear or branched alkyl radical comprising from 1 to 6 carbon atoms selected from the group consisting of methyl, ethyl, propyl, isopropyl, butyl, tert-butyl, sec-butyl, isobutyl, pentyl, neopentyl and n-hexyl radical.

39. The process as claimed in claim 22, in which $Y^3$ and $Y^4$, which are identical or different, are a linear or branched alkyl radical having 1 to 6 carbon atoms, or one of $Y^3$ or $Y^4$ is hydrogen, with the other being a linear or branched alkyl radical having 1 to 6 carbon atoms; where it is possible for $Y^3$ to form a bond with $R^3$ (or $R^3$) when E is the nitrogen atom and, in this case, $Y^4$ can also be the hydroxyl group.

40. The process as claimed in claim 39, in which $Y^3$ and $Y^4$, which are identical or different, are a methyl radical; or one of $Y^3$ or $Y^4$ is hydrogen, with the other being a linear or branched alkyl radical having 1 to 6 carbon atoms; where it is possible for $Y^3$ to form a bond with $R^3$ (or $R^{3'}$) when E is the nitrogen atom and, in this case, $Y^4$ can also be the hydroxyl group.

41. The process as claimed in claim 10, in which the amount of catalyst employed is generally between 0.0005 mol % and 2 mol %, with respect to the compound carrying the acceptor group.

42. The process as claimed in claim 17, wherein D is the residue of a cyclic compound having at least 4 atoms in the ring.

43. The process as claimed in claim 21, wherein Z in $R^5$ is sodium.

* * * * *